US006794423B1

(12) United States Patent
Li

(10) Patent No.: US 6,794,423 B1
(45) Date of Patent: Sep. 21, 2004

(54) FRACTURE-RESISTANT, CROSS-LINKED ULTRA HIGH MOLECULAR WEIGHT POLYETHYLENE SHAPED MATERIAL AND ARTICLES MADE THEREFROM

(76) Inventor: Stephen Li, 20 Banff Dr., West Windsor, NJ (US) 08550

( * ) Notice: Subject to any disclaimer, the term of this patent is extended or adjusted under 35 U.S.C. 154(b) by 0 days.

(21) Appl. No.: 09/625,713

(22) Filed: Jul. 26, 2000

Related U.S. Application Data
(60) Provisional application No. 60/146,474, filed on Jul. 30, 1999.

(51) Int. Cl.[7] .................. A61L 27/16; A61L 31/04; A61F 2/30; C08J 3/28
(52) U.S. Cl. ................ 522/157; 522/161; 523/115; 264/485; 264/488; 264/494; 264/496
(58) Field of Search ................ 522/157, 161; 523/115; 264/485, 488, 494, 496

(56) References Cited

U.S. PATENT DOCUMENTS 5,037,928 A * 8/1991 Li et al.
5,721,334 A * 2/1998 Burstein et al.
5,728,748 A * 3/1998 Sun et al. ............... 522/65
6,174,934 B1 * 1/2001 Sun et al. ............... 523/113
6,355,215 B1 * 3/2002 Poggie et al. ........... 422/23

FOREIGN PATENT DOCUMENTS

| WO | 97/29793 | 8/1997 | ........ A61L/27/00 |
| WO | 98/14223 | 4/1998 | ........ A61L/27/00 |
| WO | 98/16258 | 4/1998 | ........ A61L/2/08 |
| WO | 99/52474 | 10/1999 | ........ A61F/2/28 |

* cited by examiner

Primary Examiner—Susan W. Berman
(74) Attorney, Agent, or Firm—Greenberg Traurig, LLP.

(57) ABSTRACT

The present invention relates to a tough, wear resistant Ultra High Molecular Weight Polyethylene (UHMWPE) prepared by the cross linking of a UHMWPE shaped article with irradiation doses higher than 4 Mrads, preferably higher than 5 Mrads, and most preferably less than 10 Mrads. The invention particularly provides total joint replacement devices and methods of making them for the hip, knee, elbow and shoulder.

16 Claims, 13 Drawing Sheets

FRACTURE-RESISTANT, CROSS-LINKED ULTRA HIGH MOLECULAR WEIGHT POLYETHYLENE SHAPED MATERIAL AND ARTICLES MADE THEREFROM

This patent application claims the priority of U.S. provisional patent application No. 60/146,474 filed Jul. 30, 1999, which is incorporated herein by reference.

FIELD OF THE INVENTION

The invention relates to total joint replacement devices having improved fracture toughness, and to a method of making them. The devices can be used in total joint replacements such as hip, knee, elbow and shoulder.

BACKGROUND OF THE INVENTION

Ultra High Molecular Weight Polyethylene (hereafter referred to as UHMWPE or simply "polyethylene") has been the main material of choice as the-bearing surface in total joint replacement devices. This includes predominately hip, knee, replacements but has been used in shoulder, elbow, ankle and mandibular joint replacements. The success rate of implantation of hip and knee devices is generally quite high but the life of these devices is often limited by the wear and damage of the polyethylene components.

UHMWPE is commercially produced as a powder and is available in several grades from several companies. The grades generally differ in molecular weight and molecular weight distribution. The powder is fabricated into devices by one of three methods: (1) extrusion into bars followed by machining of the device and (2) compression molding into sheets followed by machining and (3) direct compression molding. Each method has advantages and disadvantages.

Extrusion involves introducing a fixed amount polyethylene powder into a chamber; pushing this powder into a heated cylindrical barrel with a ram which then retracts, leaving the chamber empty and waits for the next fixed amount of powder. The process is continuous and each push of the ram advances the polyethylene through the heated barrel. In this manner, the powder is consolidated into a continuous bar with typically a round cross-section. The resulting bar stock is generally from one to six inches in diameter. Implants are then machined from this cylindrical bar stock.

Compression Sheet Molding involves introducing powder into a container that can be as large as 8 inches deep, 4 feet wide and 8 feet long. A platen large enough to cover the entire container is then used to apply heat and pressure to the polyethylene in the container. Implants are then machined from this sheet.

Direct Molding is different from sheet molding in that powder is placed into a mold that compresses it into the final shape of the device without need for machining (rather than a bar or a sheet which needs to be machined into the device shape). (Some machining may be used as part of finishing operations.) The mold containing the powder is heated under pressure to consolidate the polyethylene and form the device. Devices formed in this fashion often exhibit a highly glossy surface finish. The process conditions of direct molding are often quite different from compression molding sheet and different properties are often obtained.

In total joint replacement devices, polyethylene wear and damage takes one or more of the following forms (modes): burnishing (polishing); abrasion (generation of small particles); pitting (formation of pits); delamination (loss of 'sheets' of material); and fracture.

The presence, location and extent of each of these damage or failure modes is dependent on material properties, as well as on design, kinematics, and individual patient factors.

Total Hip Replacements.

In total hip replacements, the main mode of polyethylene failure is abrasion and burnishing which generate small (<1$\mu$ diameter) polyethylene debris particles. These small particles caused by wear elicit a complex biological response which eventually leads to bone resorption which, in turn, causes implant loosening. On loosening of the implant, pain ensues and revision surgery becomes necessary. The process of bone loss due to particulate debris is termed osteolysis and is a major cause of hip replacement failure. Fractures of the polyethylene acetabular component in hip replacement devices are less common but do occur. Fracture of acetabular components has been shown to be design dependent.

Total Knee Replacements.

In total knee replacements, in addition to the generation of small debris particles, the damage to the polyethylene is often macroscopic in nature. Pitting, delamination and fracture are prevalent in total knee replacements. There have also been several reports which strongly associate pitting, delamination and fracture with decreases in polyethylene mechanical properties, specifically fracture and fatigue properties.

Previous Methods to Reduce Wear.

In the mid 1970's, Oonishi in Japan reported improvements on the wear properties of polyethylene by using high dosages of gamma irradiation. He used 100 Mrads of gamma irradiation to treat acetabular cups made from high density polyethylene for implantation. This is far above the 2.5–4 Mrads generally used to sterilize these components. This high dose irradiation causes a high degree of cross linking in the polyethylene. This cross linking has-been shown to alter many of the properties of the polyethylene, including improving the wear properties. Oonishi demonstrated a factor reduction in wear.

In the last few years, increasing cross linking levels have been revisited for the purpose of improving wear properties. There have been several reports on crosslinking achieved by either gamma irradiation or electron beam irradiation. While crosslinking has produced improvements in the wear resistance of polyethylene, it has also been shown to reduce other mechanical properties, most notably, the fracture toughness of the polyethylene. Fracture toughness of a polymer is a measure of the tendency of the material to resist fracture. A reduction in fracture toughness is undesirable because it increases the risk of fracture in acetabular cups, a catastrophic failure necessitating immediate hip surgery. Further, it is feared that decreased polyethylene toughness will significantly increase the incidence of pitting, delamination and fracture in total knee replacements or indeed in any joint replacement device where the load exceeds the yield strength of the polyethylene. Accordingly, the amount of radiation that polyethylene materials received was 4 Mrads.

Sun et al., U.S. Pat. No. 5,728,748, describes oxidation-resistant medical implants prepared from olefinic materials having a molecular weight greater than 400,000. The irradiated material is heated in an oxygen deficient atmosphere to inactivate residual free radicals.

Saum et al., U.S. Pat. No. 6,017,975, describes a process for preparing a medical implant from ultrahigh molecular weight polyethylene which is irradiated and subsequently annealed at a temperature above 150° C.

Accordingly, there is a need for polyethylene materials having both improved wear properties and not inferior fracture resistance. There is also a need for total joint replacement devices having improved wear properties such as those provided by cross linked polyethylene, without (or with less) attendant reduction in fracture toughness.

SUMMARY OF THE INVENTION

In one aspect, the invention is directed to a tough, wear resistant Ultra High Molecular weight Polyethylene shaped material prepared by the irradiation cross linking (using an irradiation dose higher than 4 Mrads, preferably 5 Mrads, and most preferably less than 10 Mrads of a UHMWPE article which has been shaped by direct compression molding. The product can used in total joint replacement devices such as hip, knee, elbow and shoulder.

In another aspect, the invention is directed to a total joint replacement device or component thereof comprising a shaped crosslinked article made from UHMWPE subjected to a process comprising direct compression molding followed with irradiation at a dose higher than 4 Mrads, preferably 5 Mrads, and most preferably less than 10 Mrads.

DETAILED DESCRIPTION OF THE INVENTION

In order to reduce the wear in total hip replacements, cross linking of UHMWPE with irradiation doses above the 2.5–4 Mrad commonly used in sterilization procedures, has been identified since the 1970's as a treatment which results in the improvement of wear resistance. The wear resistance is improved with increasing irradiation until a dose of about 100 Mrads of irradiation (and a dose of up to 200 Mrads has been used). However, cross linking also adversely affects other properties such as fracture toughness, elongation to break and yield strength. This has led to the use of doses under 10 Mrads in manufacture of joint replacement devices, i.e. doses below those at which maximum wear resistance would be obtained with a minor decrease in other properties. However, even at an irradiation dose of 10 Mrads, the decrease in fracture toughness is substantial , as shown in Table 1, below.

The reduction of these properties, in particular, fracture toughness, is believed to increase the risk of fracture- and fatigue-related failure of the polyethylene used in total joint replacement devices. This concern is particularly acute in designs or devices where the polyethylene is subjected to loads above the yield strength of the polyethylene, such as those found in total knee replacements, but may also be present for other total joint replacement devices.

The results presented here demonstrate that crosslinking of polyethylene that has been directly molded provides a material with a higher fracture toughness than that obtained by cross-linking extruded polyethylene.

This is a surprising and new finding. (In addition, although data are not shown, other mechanical properties of irradiated direct-molding products either remain the same as the mechanical properties of noncrosslinked ram-extruded (or sheet-molded) polyethylene articles or if they are adversely affected, the loss of properties of the direct-molded product is consistently less than of products made by compression sheet-molding and extruded products.)

Figure 1:
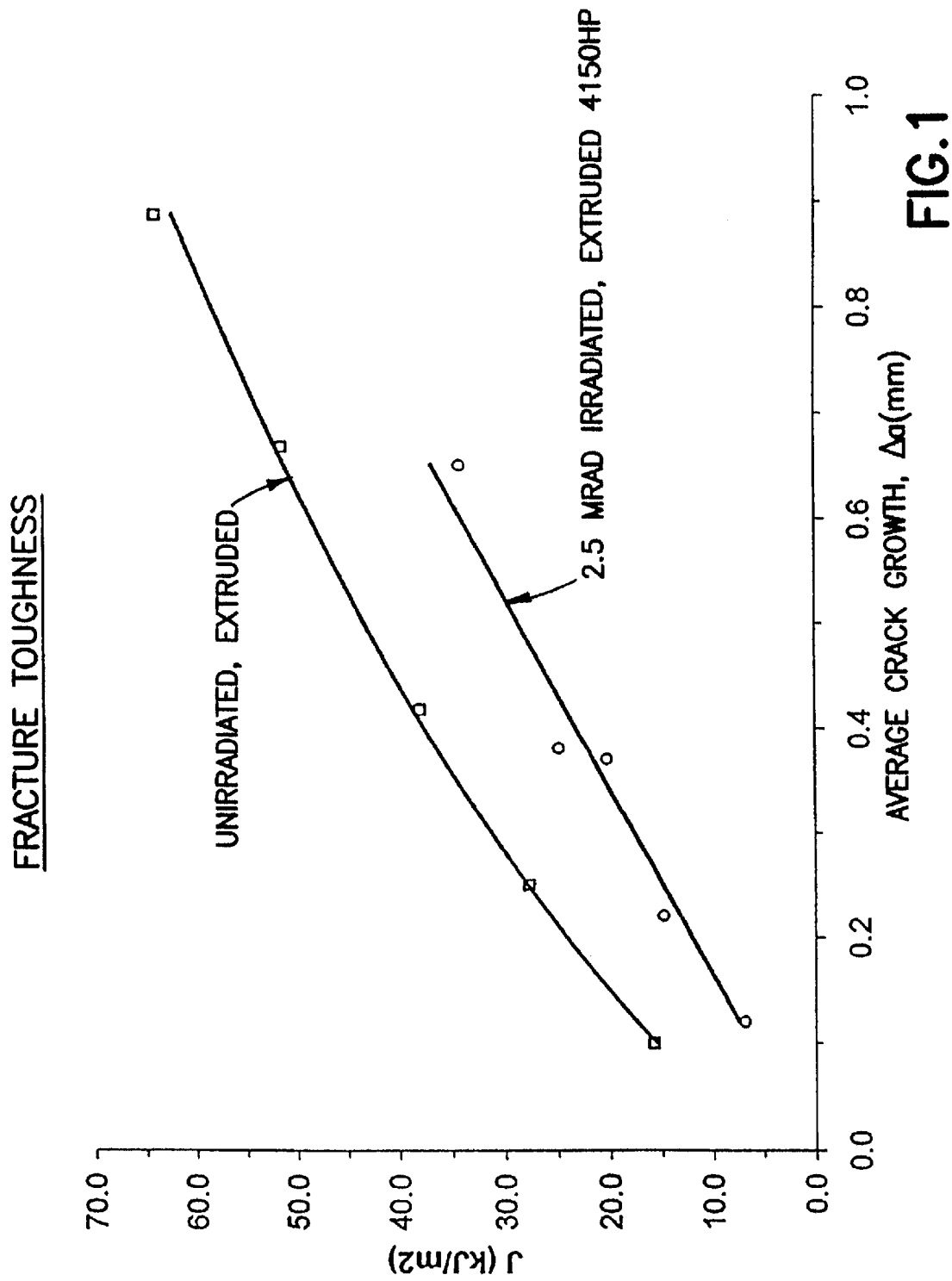
FIG. 1 is a graph of fracture toughness (J Integral curve in $kJ/m^2$) against average crack growth ($\Delta a$ in mm) for unirradiated and 2.5 Mrad gamma-irradiated samples of extruded 4150HP polyethylene rods (Group 1). The irradiated sample has lower fracture toughness because a lower energy per unit surface is required to grow a crack than in the case of the unirradiated sample.
Figure 2:
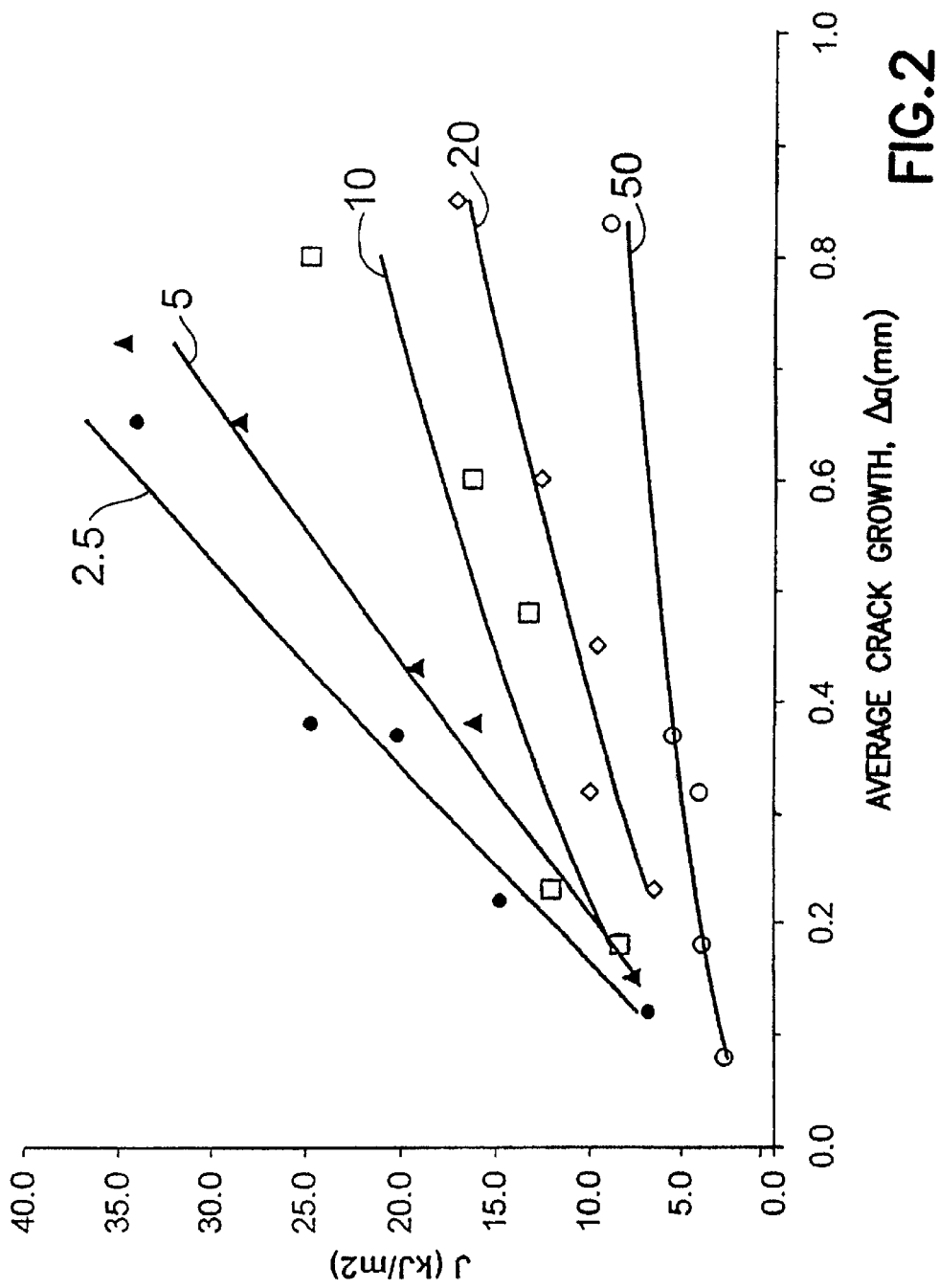
FIG. 2 is the same type of graph as FIG. 1 but depicting J integral curves for samples from Group 1 (extruded 4150HP rods) gamma irradiated at different doses from 0 to 50 Mrads. It is clear from these curves that increasing irradiation dose results in a reduction in toughness.
Figure 3:
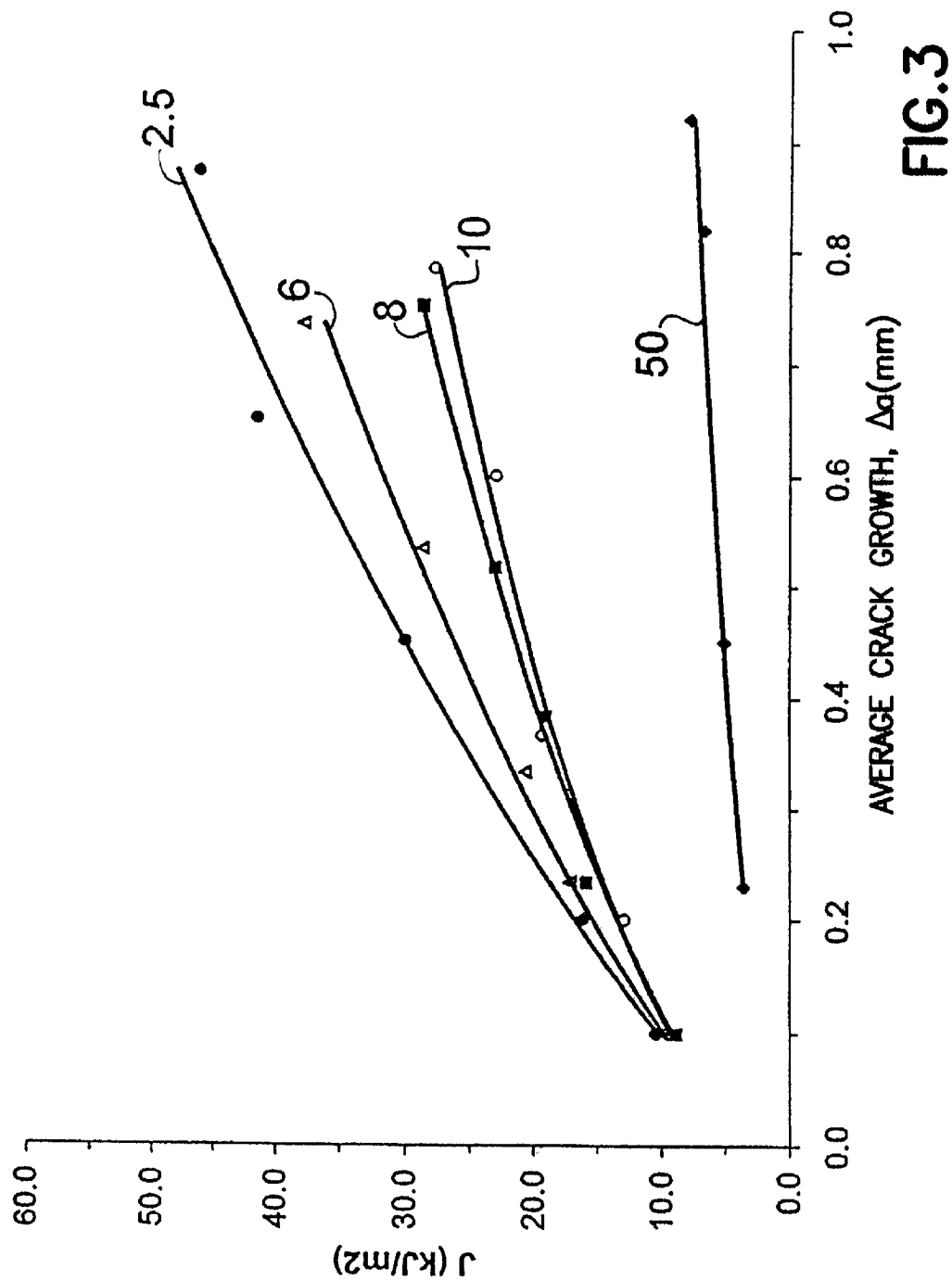
FIG. 3 is the same type of graph but depicting J integral curves for samples from Group 1A (extruded 4150HP, electron beam irradiated from 2.5 to 50 Mrads). Toughness decreases as the irradiation dose increases, similar to FIG. 2.
Figure 4:
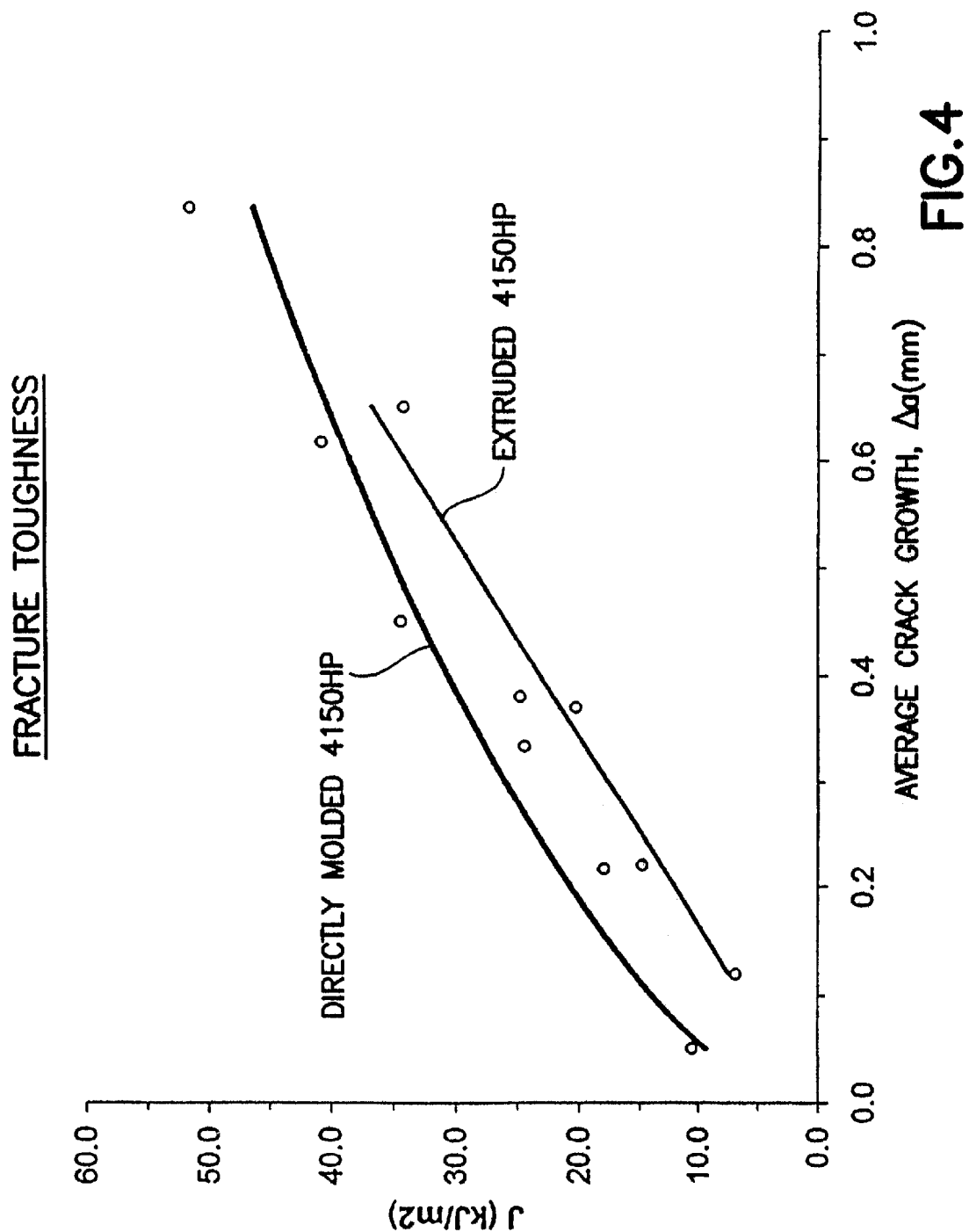
FIGS. 4 to 9 are graphs that compare the J curves for the ram-extruded samples from Group 1 with the directly molded samples of Group 2 at 2.5, 5, 10, 20 and 50 Mrads respectively. In all cases, the directly molded samples have higher J values than the ram extruded samples.
Figure 5:
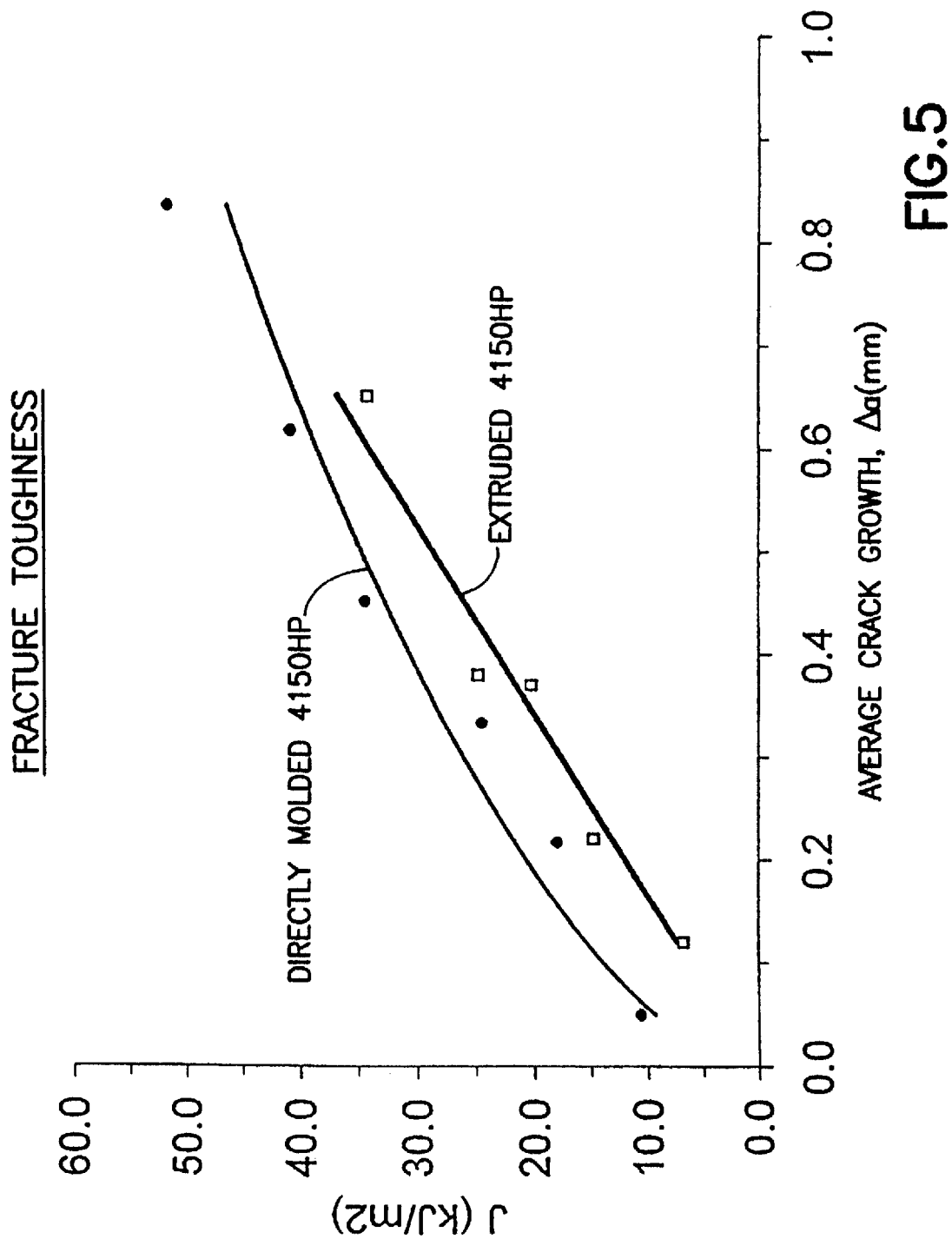
Figure 6:
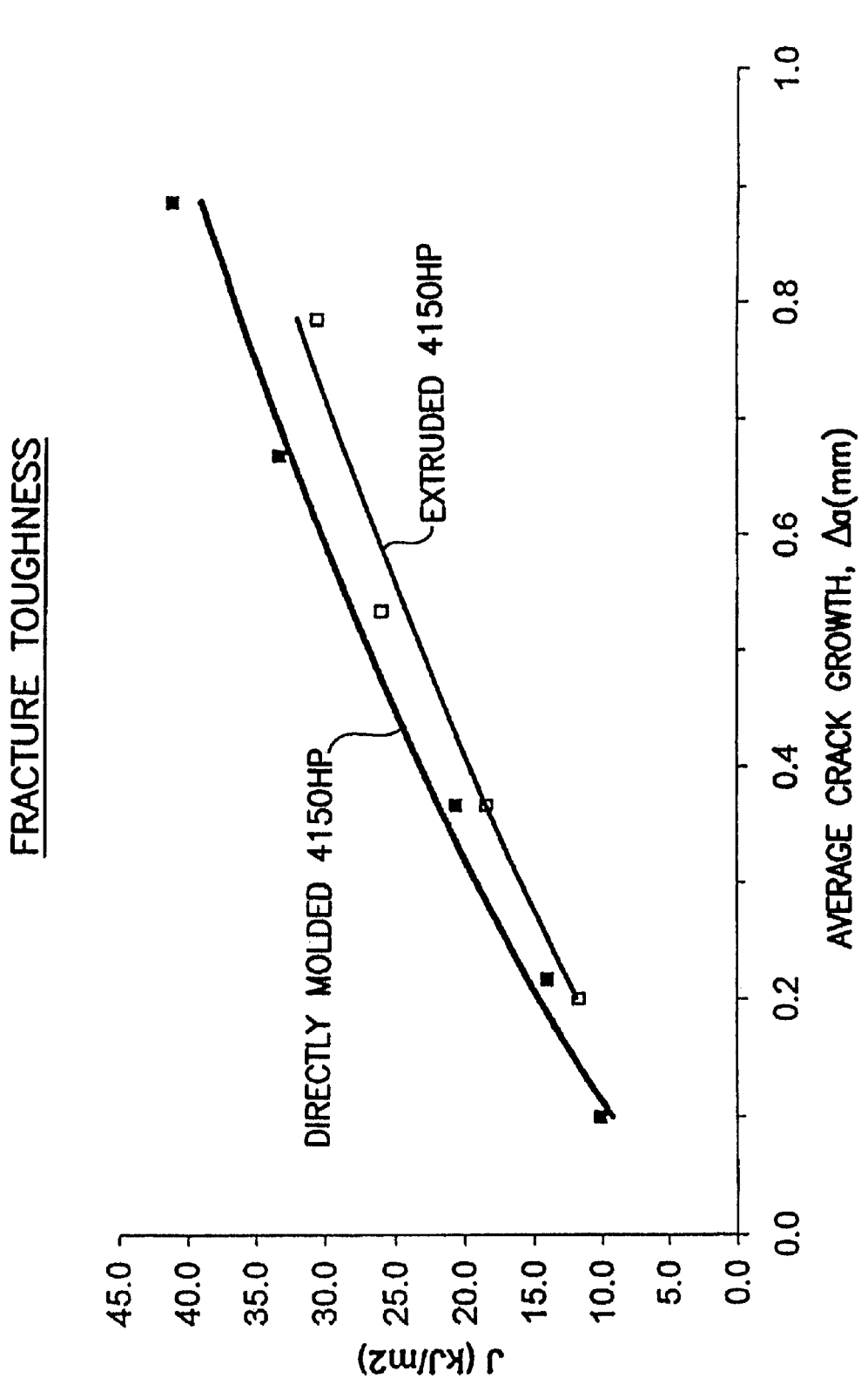
Figure 7:
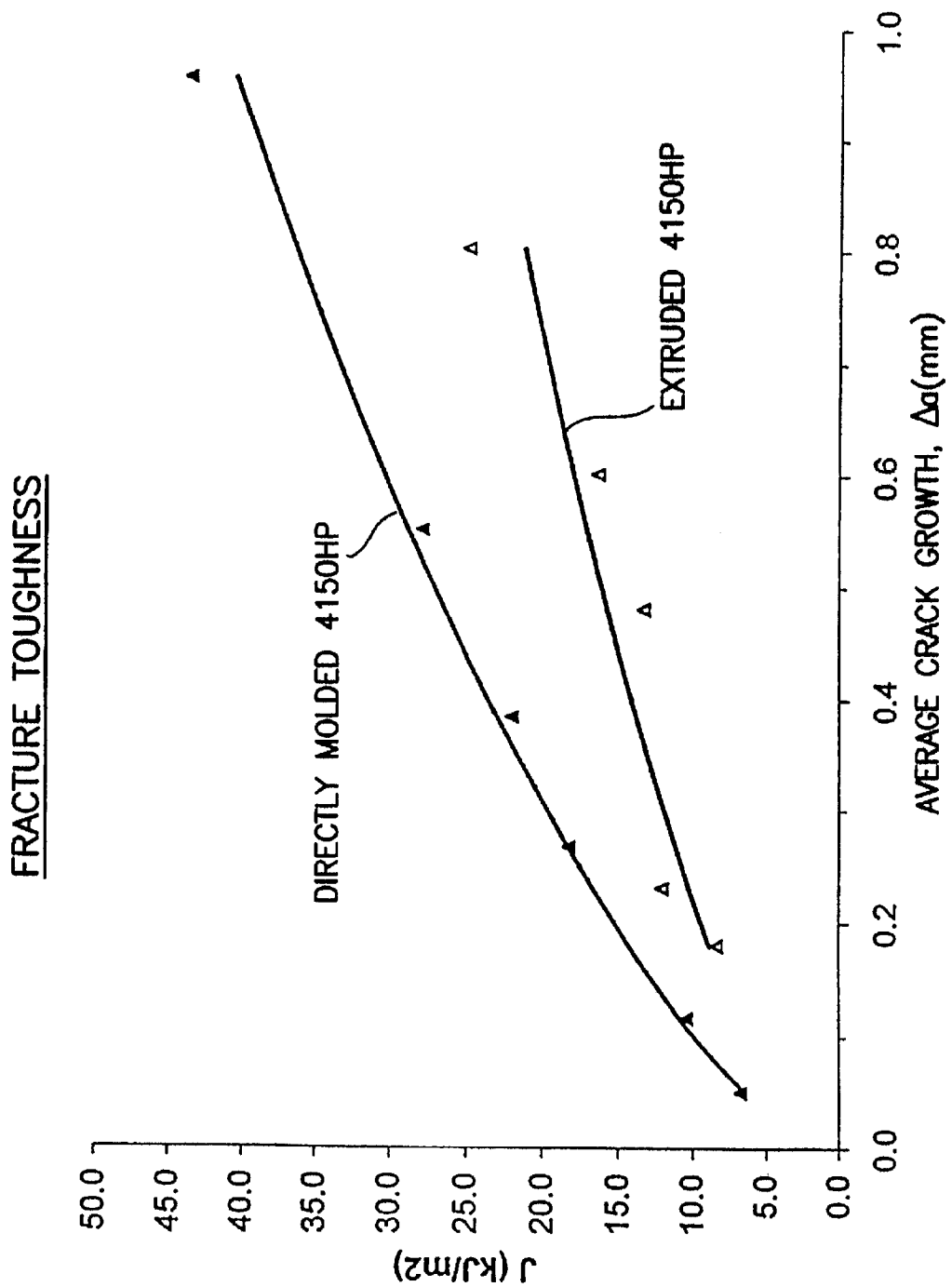
Figure 8:
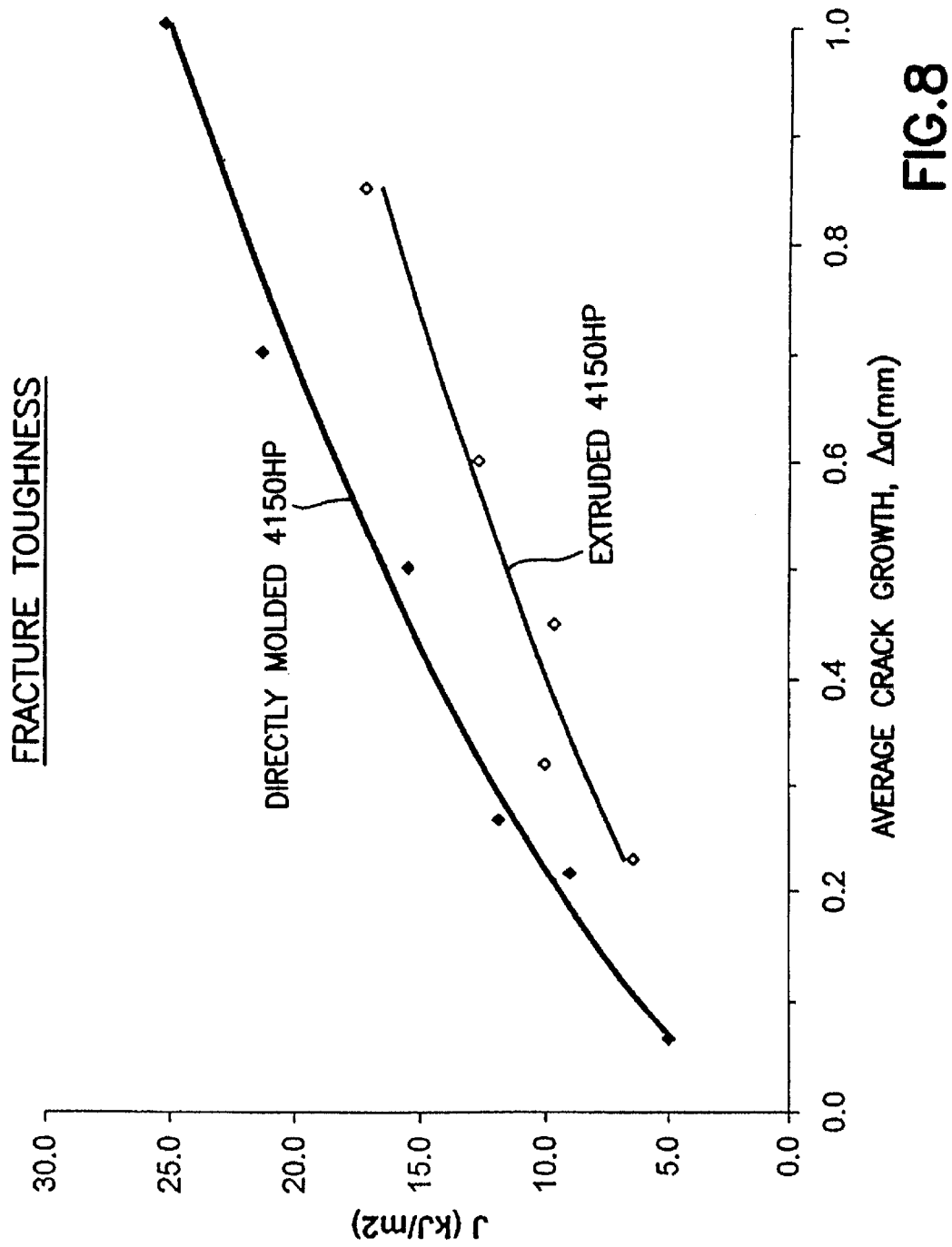
Figure 9:
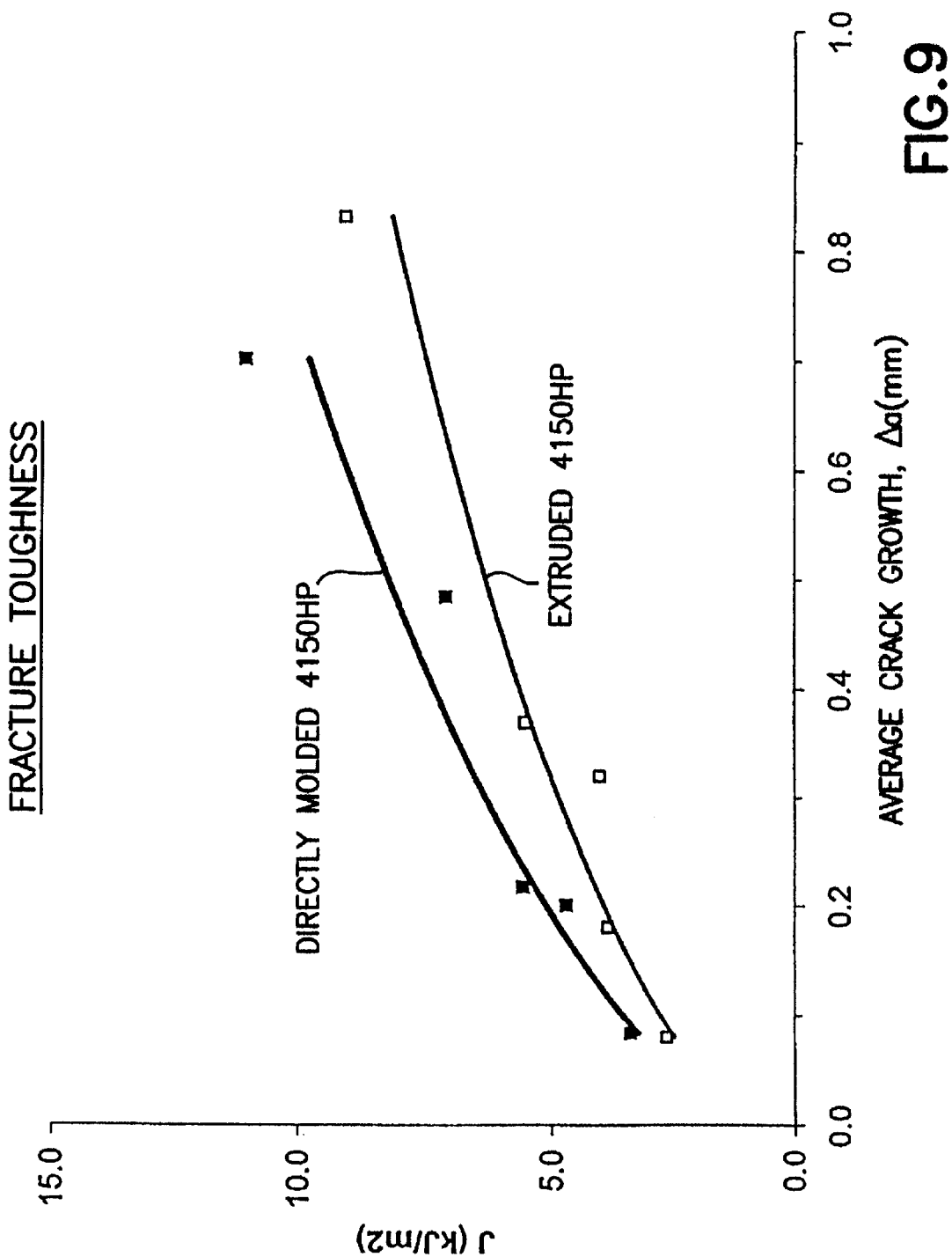
Figure 10:
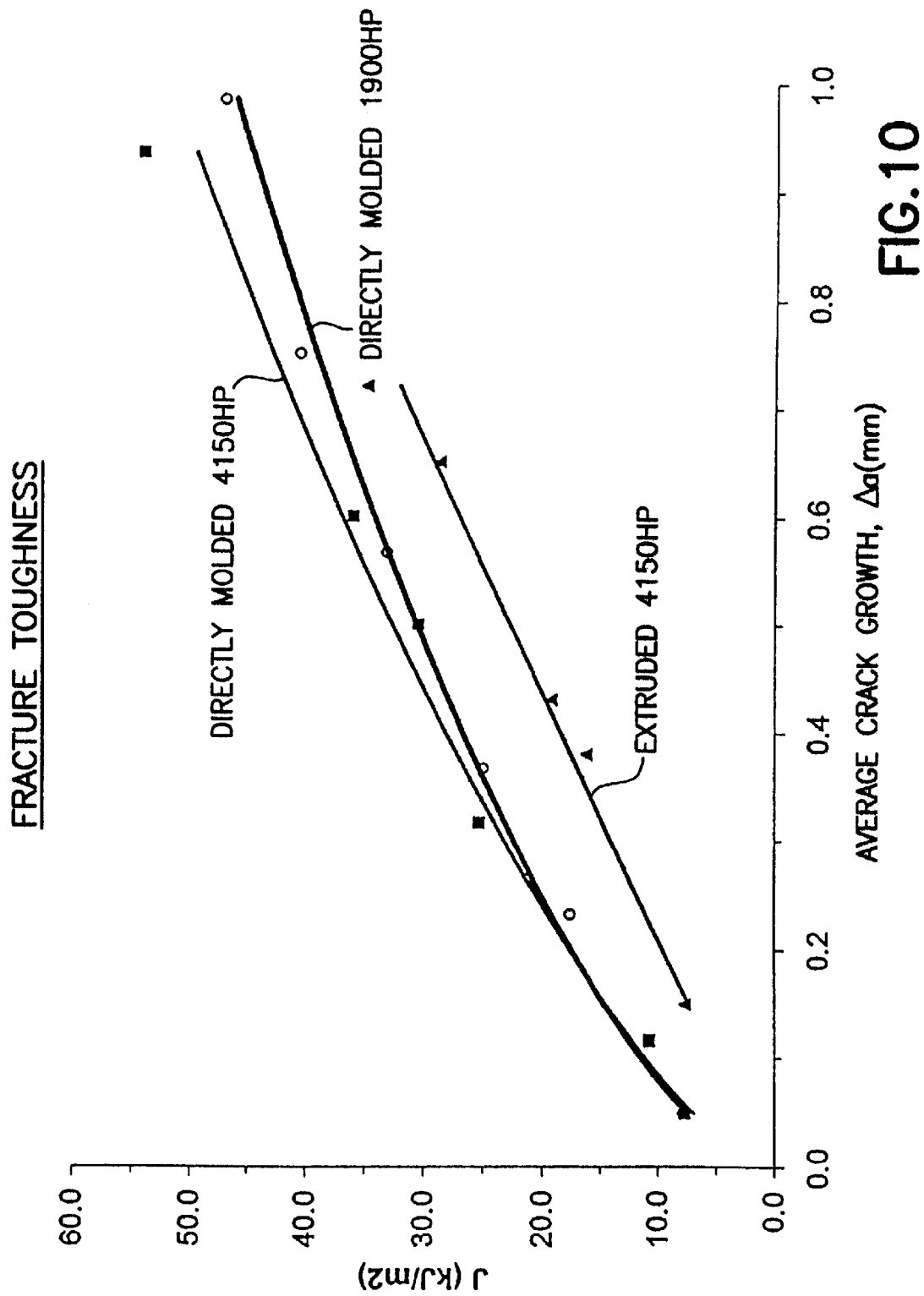
FIG. 10 is a graph that compares the J curves for (i) ram-extruded 4150HP, (ii) directly molded 4150HP and (iii) directly molded polyethylene 1900 samples after 5 Mrads of gamma irradiation. Both the molded samples, regardless of resin grade, have higher crack growth resistance than the ram-extruded sample.
Figure 11:
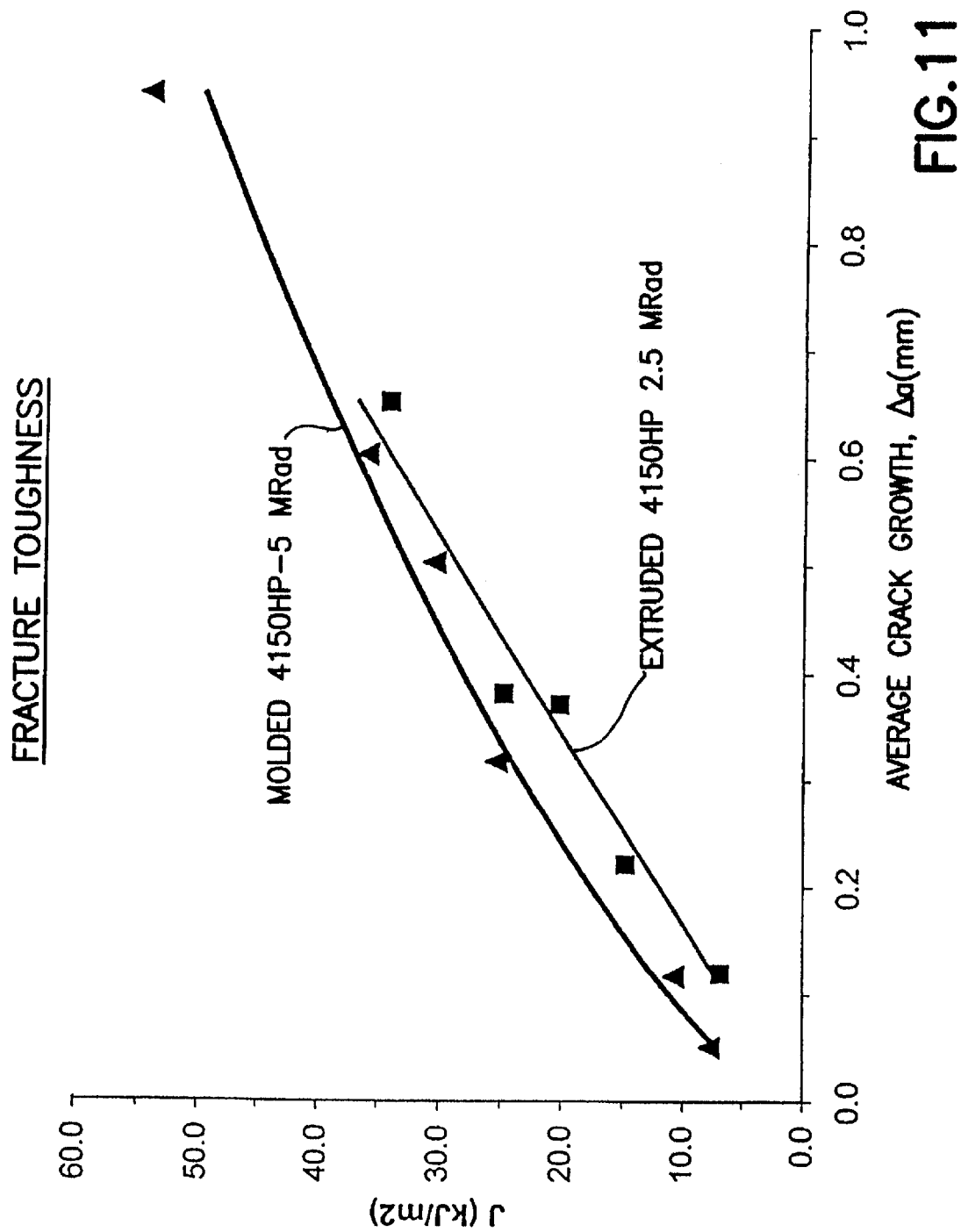
FIG. 11 is a graph that compares the J integral values for directly molded 4150HP irradiated with a higher dose (5 Mrad) with the ram extruded sample irradiated with only 2.5 Mrad. Contrary to expectation, the 5 Mrad irradiated molded sample has higher toughness than the 2.5 Mrad gamma irradiated extruded sample.
Figure 12:
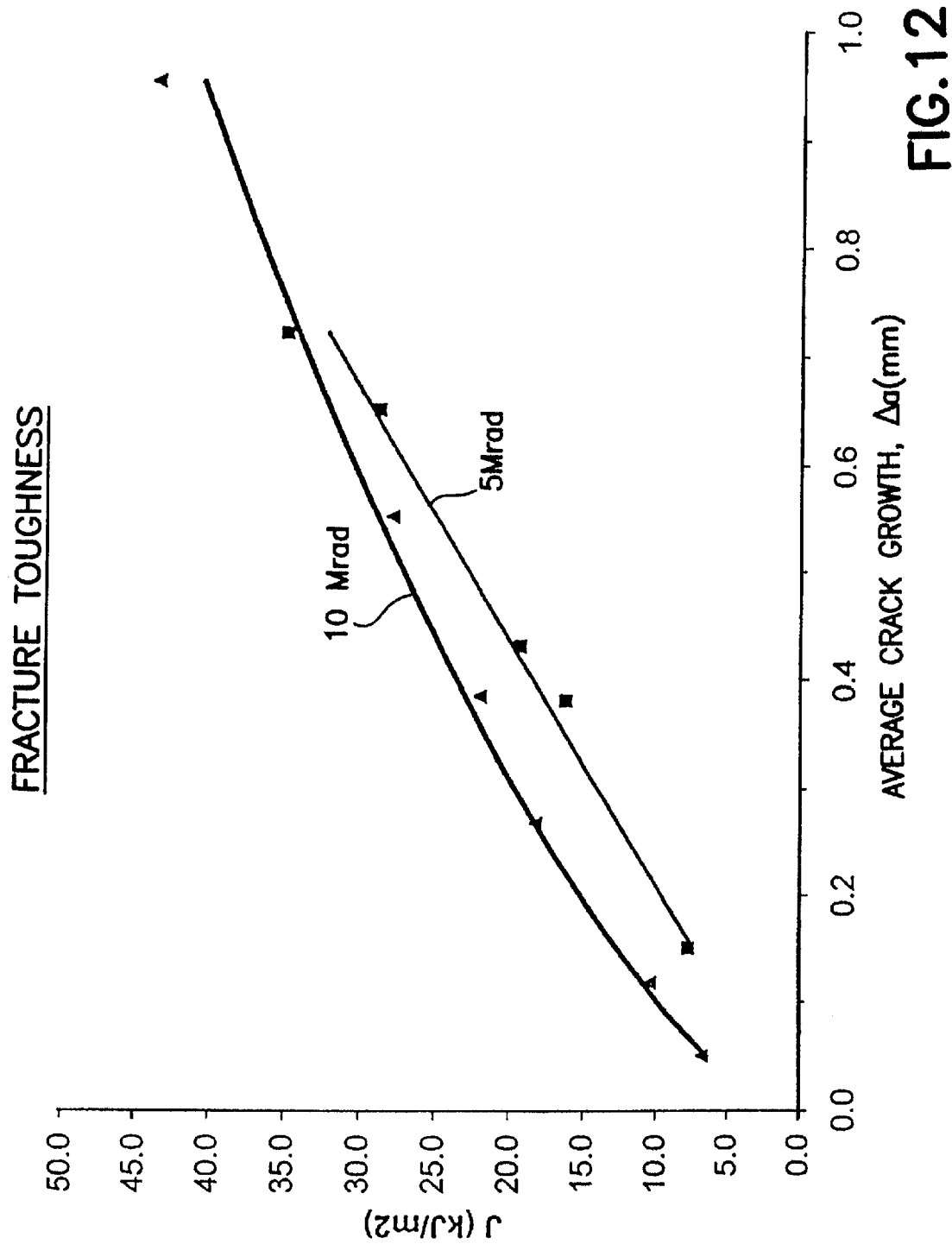
FIG. 12 is a graph that compares the J integral values for directly molded 4150HP irradiated with 10 Mrad with the 5 Mrad irradiated ram extruded sample. Contrary to expectation, the 10 Mrad irradiated molded sample has higher toughness than the 5 Mrad irradiated extruded sample.
Figure 13:
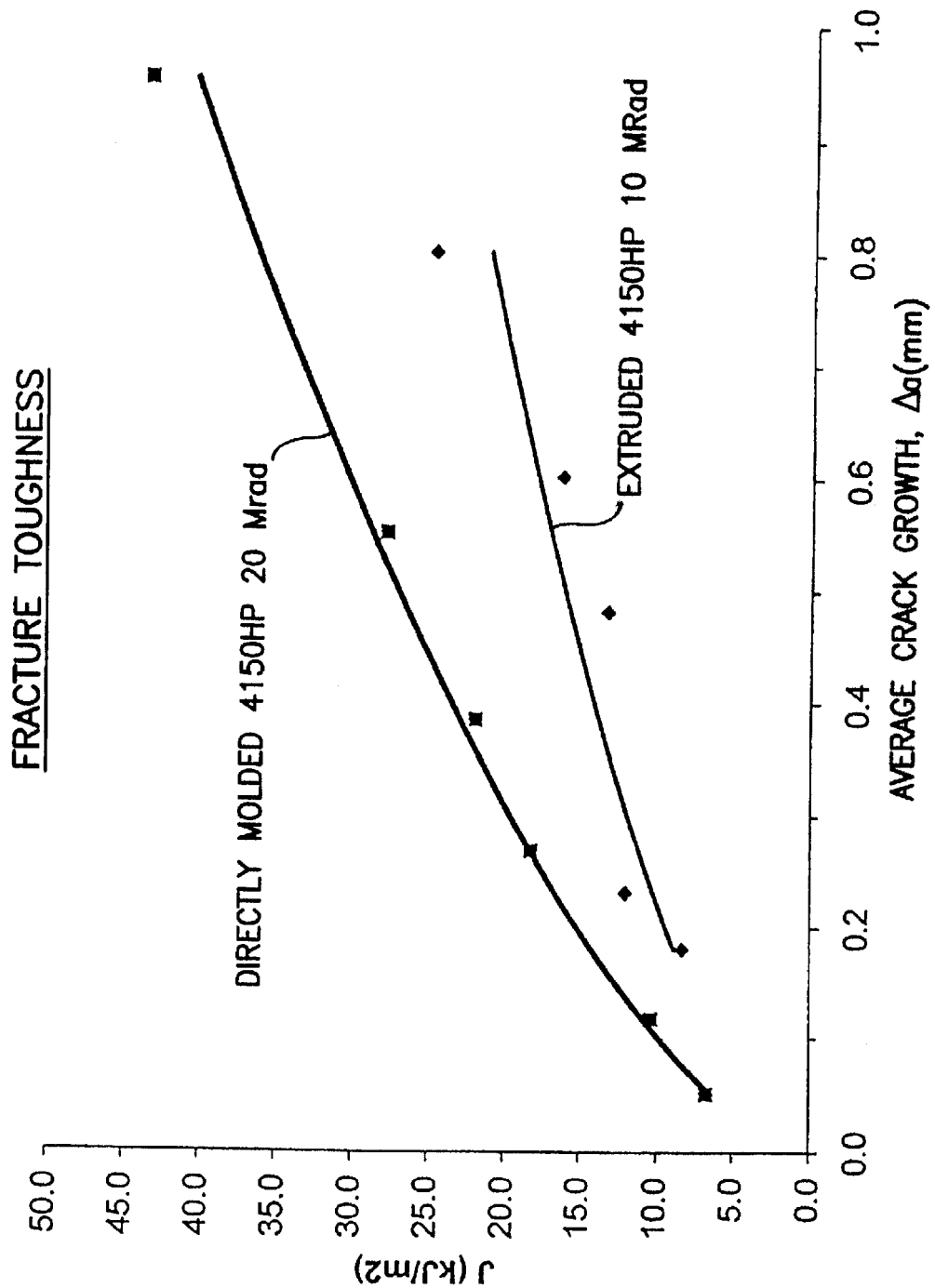
FIG. 13 is a graph that compares the J integral values for 20 Mrad directly molded 4150HP with the 10 Mrad irradiated ram extruded sample. The 20 Mrad irradiated molded sample has higher toughness than the 10 Mrad irradiated extruded sample.

At every dose from 2.5 to 50 Mrads, directly molded samples had higher toughness than the corresponding extruded (or sheet-molded) sample. The increased toughness of the directly molded samples is so significant that it is possible to use a higher irradiation dose on a direct-molded polyethylene material and still obtain a higher toughness value than the extruded material. This is shown in FIGS. 11–13. In FIG. 12, for instance, a directly molded sample irradiated at 10 Mrads has higher fracture toughness than the extruded material at 5 Mrads. This means that it is possible to obtain the wear resistance obtained by using 10 Mrads of irradiation but have virtually no fracture toughness reduction over a non-directly molded material irradiated with 5 Mrads.

Thus, it can be seen from the foregoing Figures and the Examples below that the direct molded irradiated material and articles according to the invention can withstand considerably more radiation, (thereby improving wear resistance more than the prior art) while maintaining the same fracture toughness (or even better fracture toughness) than extruded or sheet-molded materials or articles of the prior art that received considerably less radiation.

Alternatively, the, materials/articles of the invention have better toughness than their extruded or compression sheet-molded counterparts of the prior art receiving a lower radiation dose.

Direct molding techniques that can be used to make devices according to the invention are described in U.S. Pat.

No. 5,721,334, 'Process for Producing Ultra High Molecular Weight Low Modulus Polyethylene Shaped Articles Via Controlled Pressure and Temperature and Compositions and Articles Prepared Therefrom' the disclosure of which is incorporated by reference in its entirety. This patent describes use of direct molding to make ultra high molecular weight polyethylene articles with modulus values <800 MPa and as low as around 500 MPa.

The Molded Cross Linked, Low-Modulus Polyethylene materials according to the invention will preferably have oxidation resistance and low modulus (which provides for low stresses). They have a significantly improved wear resistance afforded by higher than 4, preferably at least 5, and most preferably at least 10 Mrad irradiation without significant loss of fracture toughness vs. non-directly molded counterparts. A directly molded, cross linked polyethylene with modulus <800 MPa would be advantageous in total knee replacements where the stresses are high and a decreased modulus is desirable. The upper limit of the radiation dose depends on many factors, including the degree to which the wear properties need to be improved. There have been reports in the art of doses as high as 100 Mrads or 200 Mrads, but the optimum will depend on the properties that need to be achieved, and especially the trade off that can be made between fracture toughness and wear properties.

Any type of UHMWPE polyethylene resin commonly used to make total joint replacement devices can be used to make direct-molded, irradiation-crosslinked articles according to the invention. Non limiting examples are:

| Supplier | Grade | Nominal MW | Ca Stearate Added |
| --- | --- | --- | --- |
| Ticona | 4150 | 4–6 Million | yes |
| | 4050 | 4–6 Million | no |
| | 1150 | 4–6 Million | yes |
| | 1050 | 4–6 Million | no |
| | 4120 | 2–4 Million | yes |
| | 4020 | 2–4 Million | no |
| | 1120 | 2–4 Million | yes |
| | 1020 | 2–4 Million | no |
| Montel | 1900 | 2–4 Million | yes/no |

Key for Ticona resin:
first number: 4=made in Texas 1=made in Germany
$2^{nd}$ number: 1=calcium stearate added 0=no additives
$3^{rd}$ number: 5=high molecular weight 2=lower molecular weight
$4^{th}$ number: no known meaning
1900 resin is available both with and without calcium stearate under the same number.

Additional information about-the supply of, and selection criteria for, polyethylene materials for total joint replacement devices are provided in Li, Stephen et al., *Seminars in Arthroplasty*, 9(2):105–113, April 1998; and in Li, Stephen et al., *J. Bone & Joint Surg.*, 76(A,7):1080:1090, July 1994, both incorporated by reference in its entirety.

Heating the irradiated material to the melting point of UHMWPE is not desirable and can cause deleterious effects such as causing the modulus of the irradiated material to rise above 800 MPa. Therefore, the irradiated material should not be heated above its melting point at any time. According to the present invention, no heating after irradiation is required.

Devices according to the invention can be made by methods known in the art, exemplified in U.S. Pat. No. 5,702,458, Dec. 30, 1997, Joint Prosthesis, Burstein, Albert H., et al.; U.S. Pat. No. 5,314,479, May 24, 1994, Modular Prosthesis, Rockwood Jr., Charles A., et al.; U.S. Pat. No. 4,822,364, Apr. 18, 1989, Elbow Joint Prosthesis, Inglis, Allan E., et al.; U.S. Pat. No. 4,778,475, Oct. 18, 1988, Femoral Prosthesis for Total Hip Replacement, Ranawat, Chitranjan S., et al.; U.S. Pat. No. 4,608,055, Aug. 26, 1986, Femoral Component for Hip Prosthesis, Morrey, Bernard F., et al., all of which are incorporated by reference in their entirety.

The invention is illustrated below by the following non-limiting examples.

EXAMPLES

Fracture Toughness Testing: The fracture toughness of different materials was evaluated using the J Integral method. This testing results in the generation of a curve that relates the energy required to grow a crack certain distance. The energy units are $KJ/m^2$ and the crack growth distance is in mm. The higher the J value, the tougher the material. These tests were conducted on 10×20×90 mm samples with a single edge notch, in accordance with ASTM D813-81.

Four groups of ultra high molecular weight polyethylene materials were prepared and tested: Group 1: extruded and gamma irradiated; Group 1A: extruded and electron beam irradiated; Group 2: directly molded and gamma irradiated; and Group 3: directly molded and gamma irradiated but with a different polyethylene resin grade than the other 3 groups.

Group 1:

Ram extruded 4150HP UHMWPE: gamma irradiated. The original polyethylene resin was provided by Hoechst Celanese now called Ticona (Houston, Tex.) and the ram extrusion conducted by PolyHi Solidur (Fort Wayne, Ind.). The material was then machined into J integral test specimens. At least 6 samples (10×20×90 mm) were irradiated at each of the following gamma irradiation doses: 0, 2.5, 5, 10, 20, 50 Mrads. J integral testing was conducted and the amount of energy per unit surface ($kJ/m^2$) vs Δa (change in crack length) was obtained at each dose.

Group 1A: Same material as Group 1 but electron beam irradiated. The material was then machined into J integral test specimens. At least 6 samples (10×20×90mm) were irradiated at each of the following electron beam irradiation doses: 2.5, 5, 10, 20, 50 Mrads. J integral testing was conducted and $kJ/m^2$ vs Δa (change in crack length) was obtained at each dose.

Group 2:

Directly molded 4150HP resin. The resin used was from the same lot and of the same grade used to make the ram extruded material in Group 1. Samples were prepared by direct molding 4150HP powder into 4 molds with the dimensions 10×20×90 mm. Sufficient polyethylene resin was used to ensure fully dense specimens. Stainless plates covered both surfaces of the mold. The platens of the press were heated to 165° C. and the mold was placed between the platens. The pressure was raised to 8.1 Mpa using a Carver 2699 hydraulic press for a period of time long enough to completely melt all the polyethylene powder (typically longer than 5 minutes). The pressure was released and the mold was immediately quenched in room temperature water to produce a material with modulus <800 MPa. This provided a cooling rate of approximately 175° C./minute.

At least 6 samples (10×20×90mm) were irradiated at each of the following gamma irradiation doses: 2.5, 5, 10, 20, 50 Mrads. J integral testing was conducted and kJ/m² vs Δa (change in crack length) was obtained at each dose.

Group 3:

Directly molded 1900 resin. The same molding conditions were used as for Group 2 except that 1900 UHMWPE resin (Montel, Wilmington, Del.) was used instead of 4150HP.

At least 6 samples (10×20×90mm) were obtained and irradiated at a gamma irradiation dose of 5 Mrads. J integral testing was conducted and kJ/m² vs Δa (change in crack length) was obtained.

The results are summarized in FIGS. 1–13 and Table 1 below.

Table 1 provides a comparison of J curve values (KJ/m²) associated with growing a crack 0.5 mm (Δa=0.5). The data is based on the power law fit of the curves from FIGS. 2 and 3. Note that the energy required to grow a crack of 0.5 mm decreases rapidly with increasing irradiation dosage, regardless of whether gamma or electron beam irradiation is used. At 2.5 Mrad irradiation dosage, electron beam irradiated samples are tougher (higher J) than samples that were gamma irradiated. However, at irradiation dosages greater than 2.5 Mrads, the gamma irradiated samples appear to have higher J values. Nevertheless, direct molded articles have superior toughness compared to similarly irradiated extruded or sheet-molded counterparts.

Table 1 presents KJ/m² required to grow a crack 0.5 mm as a function of irradiation dose and type for Gamma and Electron Beam Irradiated.

Ram-Extruded 4150HP Polyethylene Samples (Group 1).

| Dose | Gamma Irradiation | Electron Beam |
|---|---|---|
| 2.5 | 28.6 | 37.2 |
| 5 | 22.7 | 15.9 |
| 10 | 16.0 | 11.0 |
| 20 | 11.5 | 6.2 |

Crosslinking is determined by the final product having less than 50% extractables, as determined by ASTM D2765-90 test.

The above-mentioned patents, applications test methods, and publications are hereby incorporated by reference.

Many variations of the present invention will suggest themselves to those skilled in the art in light of the above detailed description. All such obvious variations are within the intended scope of the appended claims.

What is claimed is:

1. A joint replacement device made from ultra high molecular weight polyethylene, said material having been compressed into final shape by direct molding prior to being subjected to crosslinking irradiation as a dose higher than 4 Mrads.

2. The material of claim 1 having a modulus lower than 800 Mpa prior to crosslinking.

3. The material of claim 2, said polyethylene having a molecular weight, as determined by viscosity measurements, of greater than 1 million.

4. The material of claim 2, wherein said irradiation is selected from the group consisting of gamma and electron beam radiation.

5. A total joint replacement device comprising a material according to claim 1.

6. A total joint replacement device comprising a material according to claim 2.

7. A total joint replacement device comprising a material according to claim 3.

8. A total joint replacement device comprising a material according to claim 4.

9. A joint replacement device made from ultra high molecular weight polyethylene, said material having been compressed into final shape by direct molding and then subjected to crosslinking irradiation at a dose of at least 5 Mrads.

10. The material of claim 9 having a modulus lower than 800 Mpa prior to crosslinking.

11. The material of claim 10, said polyethylene having a molecular weight, as determined by viscosity measurements, of greater than 1 million.

12. The material of claim 10, wherein said irradiation is selected from the group consisting of gamma and electron beam radiation.

13. A total joint replacement device comprising a material according to claim 9.

14. A total joint replacement device comprising a material according to claim 10.

15. A total joint replacement device comprising a material according to claim 11.

16. A total joint replacement device comprising a material according to claim 12.

* * * * *